United States Patent [19]

Stegehuis

[11] Patent Number: 5,287,396
[45] Date of Patent: Feb. 15, 1994

[54] X-RAY EXAMINATION APPARATUS

[75] Inventor: Herman Stegehuis, Eindhoven, Netherlands

[73] Assignee: U.S. Philips Corporation, New York, N.Y.

[21] Appl. No.: 815,687

[22] Filed: Dec. 31, 1991

[30] Foreign Application Priority Data

Jan. 9, 1991 [NL] Netherlands ............... 9100019

[51] Int. Cl.$^5$ ............................................. H05G 1/64
[52] U.S. Cl. ................................ 378/98.2; 378/151; 378/152
[58] Field of Search ............. 378/99, 62, 145, 147, 378/148, 150, 151, 152, 153, 156, 159

[56] References Cited

U.S. PATENT DOCUMENTS

| | | | |
|---|---|---|---|
| 3,755,672 | 8/1973 | Edholm et al. | 250/322 |
| 4,394,738 | 7/1983 | Wagner | 364/414 |
| 4,442,489 | 4/1984 | Wagner | 364/414 |
| 4,670,896 | 6/1987 | Klausz | 378/156 |
| 4,691,335 | 9/1987 | Telorack | 378/152 |
| 4,817,125 | 3/1989 | Sklebitz | 378/152 |
| 4,935,946 | 6/1990 | Hefter et al. | 378/151 |
| 5,144,647 | 9/1992 | Kikuchi | 378/153 |

Primary Examiner—David P. Porta
Attorney, Agent, or Firm—Jack D. Slobod

[57] ABSTRACT

A contour is determined in the X-ray image by an image processing unit in an X-ray examination apparatus. An arithmetic processor responsive to the processing unit determines the position of X-ray absorbing diaphragm slats which enclose a minimum area situated around the contour of an object image. The diaphragm slats are moved to the correct position by a drive unit. As a result, overexposure of the X-ray image in the intensifier tube is counteracted and the medical details in the image become more distinct. Image harmonization are realized using X-ray absorbing wedges. Placing the wedges in excessively light parts of the X-ray image enables the dynamic range to be increased at areas of interest. The position of the wedges is calculated on the basis of a dose calculation based on exposure time, the voltage and the current applied to the X-ray source, these quantities being applied to the arithmetic processor via a control unit.

10 Claims, 2 Drawing Sheets

X-RAY EXAMINATION APPARATUS

BACKGROUND OF THE INVENTION

The invention relates to an X-ray examination apparatus, comprising an X-ray source for emitting an X-ray beam, an X-ray detector which is arranged so as to face the X-ray source and which serves to form an X-ray image of an object to be arranged between the X-ray source and the X-ray detector, a power supply system which is connected to the X-ray source for the supply of current and voltage to the X-ray source, absorption means arranged between the X-ray source and the X-ray detector to attenuate the X-ray beam, and an image processing unit which is connected to the X-ray detector in order to store the X-ray image as absorption values arranged in a matrix.

An X-ray examination apparatus of this kind is known from European Patent Specification EP-B1-157 688 which corresponds to U.S. Pat. No. 4,670,896.

The cited Patent Specification discloses that a substantial difference in contrast can occur in an X-ray image formed by exposure of an object to X-rays. These brightness differences in an X-ray image can arise because a part of the X-rays does not penetrate the object to be examined and is incident directly on the X-ray detector, or because the object to be irradiated exhibits substantial differences in absorption. For example, when in medical diagnostics an organ exhibiting a high absorption, for example a heart, is surrounded by organs which are compartively transparent to X-rays, for example lungs, an X-ray image is obtained in which the contrast within the organ of interest is low in comparison with the contrast between the brightest and the darkest areas in the overall X-ray image. In order to make the dynamic range of the X-ray image coincide as much as possible with the contrast between the brightest and the darkest areas in the organ of interest, absorption means are arranged in known manner between the X-ray source and the object to be irradiated. To this end, there is made a first X-ray exposure which is projected as an optical image onto the object, via an X-ray image intensifier, a television camera device which cooperates with an exit window of the X-ray image intensifier, and a projection device. Subsequently, the absorption means, having an optical absorption proportional to their absorptive power for X-rays, are manually introduced into the light beam of the projected X-ray image, thus achieving a desired reduction of the dymamic range of the X-ray image. Such a method for positioning the absorption means necessitates the use of an additional projection device, increasing the complexity of the X-ray examination apparatus, and is comparatively cumbersome because of the manual operations involved. Moreover, because of the difference in interaction of X-rays and light with matter, a desired X-ray attenuation is merely approximated when the absorption means occupy a position producing a desired optical attenuation.

SUMMARY OF THE INVENTION

It is an object of the invention to provide an X-ray examination apparatus in which the absorption means are accurately positioned and overexposed areas in the X-ray image are reduced. It is another object of the invention to provide an X-ray examination apparatus in which a contrast in an X-ray image is accurately limited to predetermined limits. To achieve this, an X-ray examination apparatus in accordance with the invention is characterized in that the image processing unit comprises detection means for detecting sub-areas in the X-ray image within which the absorption values are below a predetermined threshold value, and arithmetic means for calculating a position of the absorption means in which they increase the absorption values in the sub-areas of the X-ray image to a predetermined value, the image processing unit being connected to a drive unit for displacing the absorption means to the position calculated by the image processing unit.

The invention is based on the recognition of the fact that, when a part of the X-ray beam is incident of the X-ray detector without having penetrated an object arranged between the X-ray source and the detector, the X-ray image will comprise a distinct contour within which a projection image of the irradiated object is visible and beyond which the X-ray image is overexposed. Automatic detection of this contour is realized, for example by determining the gradient in each point of the X-ray image or by image segmentation of the basis of a threshold value, the threshold value being, for example a fraction of the maximum absorption value. Via detection of the contour, the position of the absorption means in the X-ray beam can be calculated in which the overexposed areas in the X-ray image are masked, after which this position can be automatically adjusted. The visibility of the relevant details is thus improved, because the overexposed areas can no longer detract an observer and because on average the scattered radiation is less because of the reduction of the X-ray beam. When an X-ray image intensifier is used as the X-ray detector, the "veiling glare" in the image intensifier and the optical system decreases when the absorption means are suitably positioned. The "veiling glare" is caused by scattered X-rays and scattered electrons and photons in the X-ray image intensifier and appears as a veil across the X-ray image. Besides the positioning of the absorption means outside the contour in the X-ray image, it is usually advantageous to enhance the contrast of sub-areas situated within the contour of the X-ray image by reducing the dynamic range of the sub-areas relative to one another. To this end, sub-areas which are too light can be automatically determined and the position of an absorption member having a locally varying absorption, for example a radiation-absorbing wedge, can be automatically adjusted. This adjustment can be accurately performed by calculation of the overall absorption of the object and the absorption means.

By automatic positioning of the absorption means which may fully absorb or partly transmit X-rays, the positioning in the first case being based on contour determination and in the second case on absorption calculation, optimum adjustment for these means can be quickly obtained. This enhances the ease of operation of the X-ray examination apparatus and the quality of the X-ray images.

An embodiment of an X-ray examination apparatus in accordance with the invention is characterized in that the absorption means are substantially non-transparent to X-rays, the detection means comprising a contour calculation unit for calculating a contour of a sub-area in the X-ray image, the arithmetic means being suitable for calculating a smallest projection of the absorption means in the X-ray image within which the contour is situated.

The position in which the absorption means enclose the smallest X-ray beam can be determined by calculating, using the arithmetic means and for different positions of the absorption means, the projection of the absorption means in the X-ray image where the projection is situated fully outside the contour. This is the optimum position of the absorption means, which optimum position is adjusted via the drive unit.

An embodiment of an X-ray examination apparatus in accordance with the invention is characterized in that the absorption means comprise a first pair of slats having parallel, straight sides and being situated in a first plane extending transversely of the X-ray beam, the slats being translatable in the first plane in a direction transversely of the sides and being rotatable together in the first plane about an axis of rotation, and also comprise a second pair of slats having parallel, straight sides and being situated in a second plane which extends parallel to the first plane the second pair of slats being translatable in the second plane in a direction transversely of the sides and being rotatable about the axis of rotation in the second plane.

An optimum position of the absorption means is found, for example by determination, in the X-ray image, of points of intersection of the contour and a first line extending through the center of the X-ray image, the points of intersection being given by coordinates in the matrix of absorption values stored in the image processing unit. For a second line extending through a point of intersection found and perpendicular to the line through the center and the relevant point of intersection, it is determined whether it intersects or is tangent to the contour in a further point. If the contour is intersected by the second line, the same procedure is repeated for a further line which extends parallel to the second line but which is situated nearer to the edge of the image; this is continued until the line is found which extends perpendicular to the first line and which is tangent to the contour without intersecting the contour. Thus, for different angular positions of the first line through the center pairs of parallel tangents are calculated which extend perpendicular to the first line and which are tangent to the contour. By determination of the two pairs of tangents enclosing the smallest area, the position of the absorption means in which the projection of the sides of the slats coincides with the tangents found is found as the optimum position of the absorption means. The drive unit rotates the absorption means through the angle which is equal to the angle of the normal to the tangent pairs found in the coordinate system defined by the image matrix, the translation of the slats by the drive unit being proportional to a distance between the line pairs and the centre of the X-ray image.

A further embodiment of an X-ray examination apparatus in accordance with the invention is characterized in that the absorption means comprise a circular diaphragm.

In that case an optimum position of the absorption means is determined, for example by the smallest circle circumscribing the contour in the X-ray image and having the center of the X-ray image as its center.

A further embodiment of an X-ray examination apparatus in accordance with the invention, in which the absorption means comprise an absorption member exhibiting a locally varying absorption, is characterized in that the power supply system is connected to a control unit for adjusting the voltage and current generated by the power supply system during an exposure time, the image processing unit being connected to the control unit in order to receive the adjusted exposure time value, the voltage value and the current value, and to apply these values to the arithmetic means in order to determine the position of the absorption means.

On the basis of the current and the voltage in the X-ray source and the exposure time, the energy fluence of the X-rays emitted by the X-ray source can be calculated in the control unit. During irradiation of the object, the X-ray beam is attenuated by interaction with the atoms in the object, which interaction may be a photoelectric effect or a Compton or Rayleigh scattering. An X-ray which is not detected by the X-ray detector after scattering contributes to the contrast in the X-ray image, whilst an X-ray which is detected after scattering adversely affects the contrast. The scattering of X-rays is dependent on the thickness of the irradiated object. Due to the scattering, for the energy fluence detected by the detector it holds that:

$$\phi_d \cdot \phi_o \, k(x) e^{-\mu x} \qquad (1)$$

where x is the thickness of the irradiated object, $\phi_o$ is the energy fluence from the source, and $\mu$ is the linear attenuation coefficient for X-rays. The factor $k(x)$ represents the contribution of the scattered X-rays to the detected energy. The factor $k(x)$ is dependent on the object thickness x, on the geometry of the X-ray examination apparatus, and on the possible presence of a scatter grid in front of the X-ray detector. Using equation (1), the thickness of the irradiated object can be calculated from the measured energy fluence $\phi_d$ and from $\phi_o$ which is calculated from the exposure time and the voltage and current applied to the X-ray source. Subsequently, the overall thickness of the object and the absorption means for which a desired attenuation occurs in the X-ray image can be calculated. Because the scattering of the X-rays in the absorption means is also determined by this calculation, the effect of the position of the absorption means on the contrast in the X-ray image is comparatively accurately known.

BRIEF DESCRIPTION OF THE DRAWING

Some embodiments of an X-ray examination apparatus in accordance with the invention will be described in detail hereinafter, by way of example, with reference to the accompanying drawing. In the drawing.

DESCRIPTION OF THE PREFERRED EMBODIMENT

Figure 1:
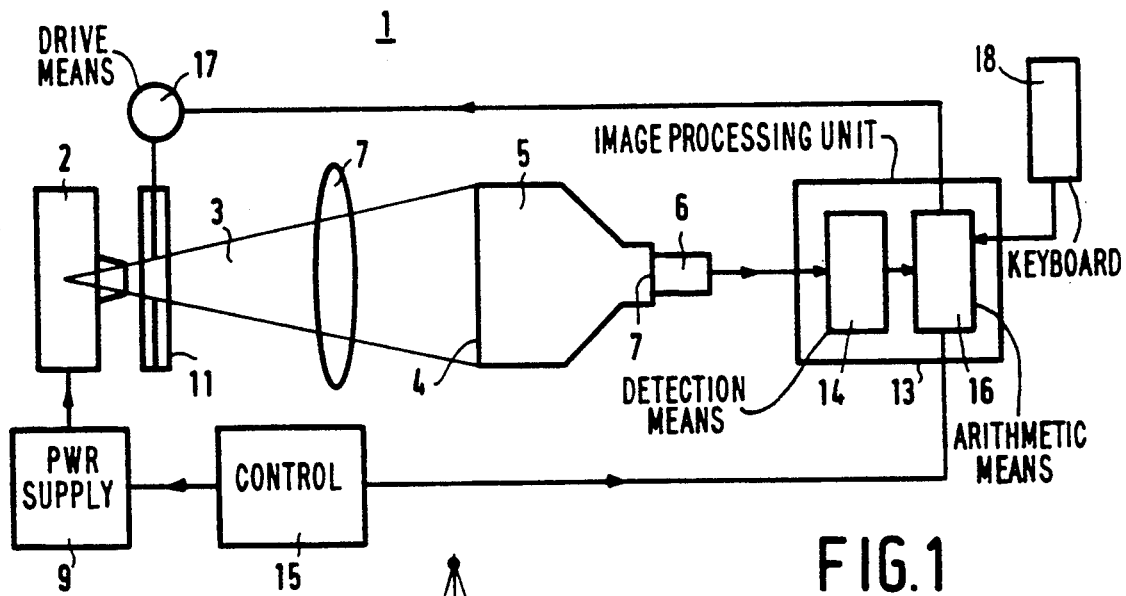
FIG. 1 is a diagrammatic representation of an X-ray examination apparatus for medical diagnostic purposes according to an embodiment of the present invention.

FIG. 1 shows an X-ray examination apparatus 1 for medical diagnostic applications, for example fluoroscopy or angiography. From a focus an X-ray source 2 generates a beam of X-rays 3 which passes through absorption means 11 which is incident on an X-ray detector 5 via object 7. Due to absorption differences in object 7, the X-ray beam is locally intensity modulated so that a projection image of the object 7 appears on an entrance screen 4 of the X-ray detector 5. The X-ray detector 5 is in this case an X-ray image intensifier in which X-rays produce light in an entrance screen consisting of CsI, so that the X-ray image is converted into an optical image. In a photocathode the optical image releases electrons which are accelerated to, for example 20 keV by means of an electrode system and which are focused on an exit screen 7 of the X-ray image intensifier 5 on which a phosphor layer is provided. A reduced and brightness-intensified image of the entrance screen 4 of the X-ray image intensifier 5 appears on the exit screen 7. Via a television camera tube 6 which cooperates with the exit screen 7 of the X-ray image intensifier 5, the optical image is converted into an electric signal which is applied to an image processing unit 13 via image detection means 14. In the image processing unit 13 the signals from the television camera tube 6 are digitized and stored in the form of a matrix of grey values. X-ray image detection means 14 in response to the electrical signal from tube 6 determines a contour beyond which the grey values exceed a given threshold value. A means 16 calculates a position of the absorption means 11 in which the area outside the contour in the X-ray image is masked as much as possible by the absorption means 11. The arithmetic means 16 subsequently controls drive means 17 to move the absorption means 11, in this case absorbing the X-rays completely, to the desired position. In addition to the limitation of the X-ray beam 3 by the absorption means 11, it may be desirable to introduce absorption means 11 into the beam so as to attenuate the beam at predetermined locations. To this end, the arithmetic means 16 are connected to a control unit 15 which controls a power supply system 9 and which adjusts an exposure time, voltage and current of the X-ray source 2. The arithmetic means 16 can receive, for example via a keyboard 18, information concerning the distance between the focus of the X-ray source 2 and the entrance screen 4, the image reduction factor of the X-ray image intensifier 5, and the aperture of a diaphragm (not shown in the Figure) arranged between the exit screen 7 and the television camera tube 6. On the basis of inter alia the exposure time, the voltage and the current in the X-ray source 2, the arithmetic means 16 calculate a desired position of the absorption means 11 which in this case comprise, for example a Perspex wedge, e.g., thermoplastic material wedge.

Figure 2:
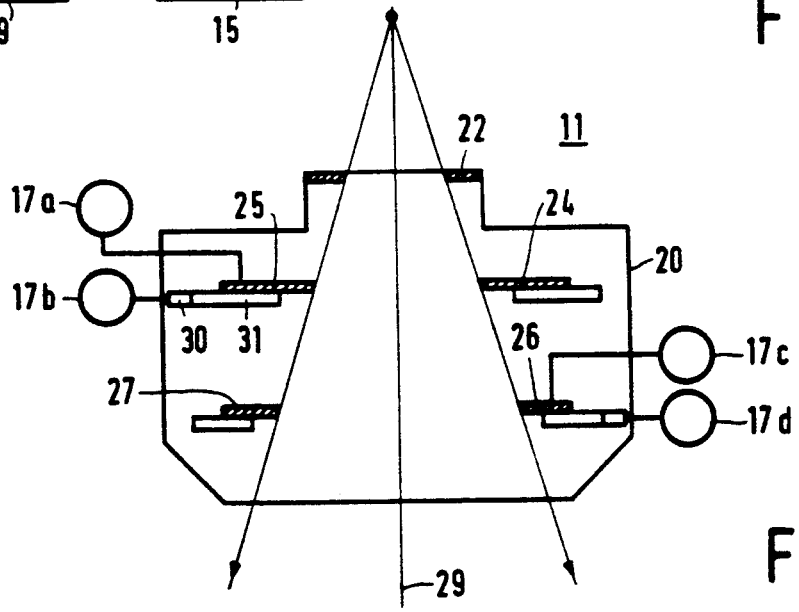
FIG. 2 is a partially diagrammatic and partially in section side elevation view of an embodiment of an absorption structure used in the embodiment of FIG. 1.

FIG. 2 diagrammatically shows the absorption means 11, an iris diaphragm 22 and lead slats 24, 25, 26 and 27 mounted in a housing 20. The drive means 17 is formed by four step motors 17a, 17b, 17c, 17d. Via a step motor 17a, the lead slats 24 and 25 can be displaced together in the direction of the axis 29, in this case the position of the lead slats 24 and 25 being symmetrical with respect to the axis 29. Via a step motor 17b, driving a rotary member 31 via a gear wheel 30, the lead slats 24 and 25 can be rotated about the axis 29. A similar construction is provided lead slats 26 and 27.

Figure 3:
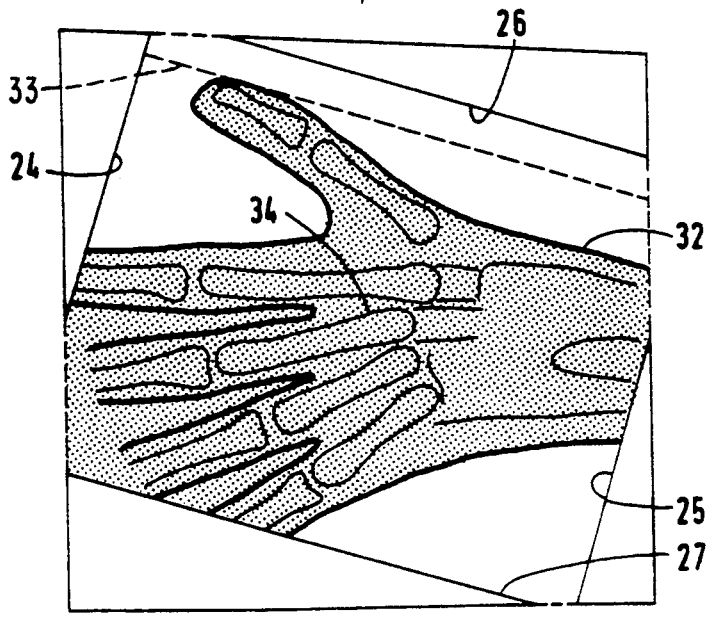
FIG. 3 illustrates imaging a hand with the embodiment of FIGS. 1 and 2.

FIG. 3 shows an X-ray image of a hand, the areas situated outside the contour 32 being overexposed because the X-rays are incident on the X-ray image intensifier 5 without having been attenuated. When the lead slats 24, 25, 26 and 27 are arranged in the positions shown, in which in the present example a distance from an image center 34 is the same for the masking lead slats 24, 25, 26 and 27, overexposure is substantially prevented. When the lead slats 24, 25, 26 and 27 are independently displaceable with respect to the image center 34, a position of the lead slat 26 along a line 33 is optimum. In this case a step motor 17 is provided for displacement of each lead slat.

Figure 4:
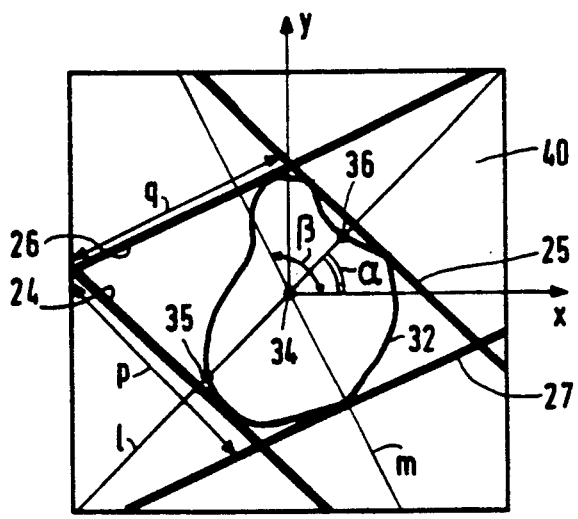
FIG. 4 is a diagram useful for explaining certain principles of the present invention.

FIG. 4 diagrammatically illustrates the calculation of an optimum position of the lead slats 24, 25, 26 and 27 by arithmetic means 16. After determination of the contour 32 in the digital image matrix 40 by the contour calculation unit of arithmetic means 16, the intersection with the contour 32 is determined along a line l which extends through the image center 34 and which encloses an angle $\alpha$ with respect to the x-axis. From the points of intersection 35 and 36 it is determined, along a line extending perpendicular to l, whether more than one point of the contour is situated on this line. If so, this operation is repeated for a further line which extends perpendicular to l but which is situated nearer to an edge of the image. Thus, the positions of the lead slats 24 and 25 are found. The same procedure can be followed for a line m which encloses an angle $\beta$ with respect to the x-axis, resulting in the positions of the lead slats 26 and 27. The area enclosed by the lead slats in this position is given by q.p. sin ($\beta$-$\alpha$). Therein, q and p are the length of the sides of the rhombic projection of the lead slats 24, 25, 26 and 27. By calculating the surface area at a given angle $\beta$ for a number of (for example, 90) angles $\alpha$, a setting can be found for the lead slats 24, 25, 26 and 27 in which the surface area is minimum. After the smallest surface area has been found, the lead slats are rotated through the desired angles $\alpha$ and $\beta$ about the axis 29, after which they are displaced with respect to the center of the X-ray image.

Figure 5:
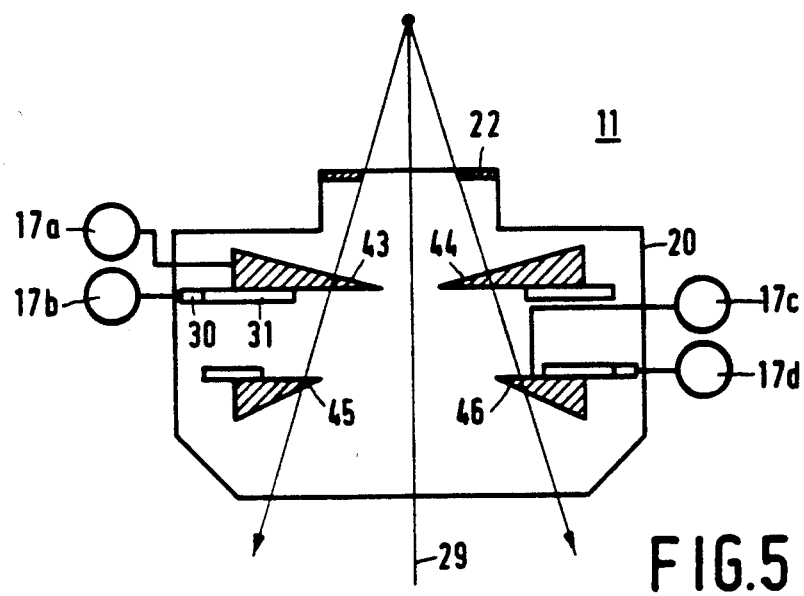
FIG. 5 illustrates a partially diagrammatic and a partially in section elevation view of a second embodiment of the invention.

FIG. 5 shows the absorption means 11, the lead slats being replaced by absorption members 43, 44, 45 and 46 having a varying absorption, for example Perspex wedges. The rotation of the wedges 43, 44, 45 and 46 about the axis 29 can be coupled, so that one of the step motors 17b and 17d for driving the rotation can be dispensed with. These absorption means enable elimination of differences in intensity of sub-areas situated within the contour 32 as shown in the FIGS. 3 and 4. To this end, the arithmetic means 16 of the image processing unit 13 calculate the energy fluence $\phi_o$ from the preset values of the exposure time, the voltage and the current of the X-ray source as:

$$\phi_o(df) = 36 \text{ J.tirr.}(T/100)^{2.1}/df^2 \qquad (2)$$

Therein:
df is the distance between the point at which the energy fluence is observed and the focus of the X-ray source 2 in m;
tirr is the exposure time in s;
J is the current from the cathode to the anode in the X-ray source in mA;
T is the maximum voltage at which the electrons in the electron source are accelerated in kVp;
$\phi_o$ is given in nJmm$^{-2}$ Without taking into account scattered radiation, after irradiation of an object having a thickness $x_p$ and an absorption coefficient $\mu$ (m$^{-1}$) the energy fluence $\phi_d$ on the detector is:

$$\phi_o(df) = \phi_o(df) \, e^{-\mu x_p} \quad (3)$$

Using this equation, the thickness $x_p$ of the irradiated object can be found by substitution of the value for $\phi_o(df)$ found by way of the equation 2. When the absorption values are too low within a sub-area of the X-ray image and the energy fluence on the detector is to be reduced to $\phi_d'(df)$ by way of a filter having a thickness $x_f$, the filter thickness is simply found from the relation:

$$\phi_d'(df) = \phi_o(df) \, e^{-\mu_p x_p - \mu_f x_f} \quad (4)$$

The dynamic range of the X-ray detector can be more effectively used by translation of an absorbing wedge in the X-ray beam to the position in which the projection of the part of the wedge having a thickness $x_f$ coincides with the excessively bright sub-area in the X-ray image.

Using a simple model for X-ray attenuation by an object as described above, the relation between the energy fluence detected by the detector and the thickness of the irradiated object usually cannot be determined sufficiently accurately. The dependency of the attenuation coefficient $\mu$ on the acceleration voltage of the X-ray source, scattered radiation effects and possible presence of a scatter grid between the irradiated object and the X-ray detector have an effect on the energy fluence measured by the detector. The attenuation coefficient $\mu$ can be written as:

$$\mu = t + s \quad (5)$$

Therein, t is the contribution by the photoelectric effect to the attenuation and s is the contribution by the scattering to the attenuation. s is constant, while t may be written as:

$$t = t_{ref}(T/E_{ref})^{-2.75} \quad (6)$$

Therein, $t_{ref}$ is a calibration value of the attenuation due to the photoelectric effect for the energy $E_{ref}$, the values amount to, for example: $t_{ref} = 0.0008$ m$^{-1}$ for $E_{ref} = 100$ KV. Furthermore, between the source and the object to be irradiated prefiltering takes place by means of Al of Cu filters in order to filter the low-energetic X-rays which do not contribute to imaging out of the X-ray beam. When an object is irradiated, the absorption of the low-energetic X-rays in the object is greater than the absorption of the high-energetic X-rays, so that the mean energy of the X-ray beam increases as the object is penetrated further by the X-rays (beam hardening). A formule which comparatively accurately describes the energy fluence $\phi_p$ behind a number of i irradiated objects (filters, object to be examined, etc.) is as follows:

$$\phi_p(df) = \phi_o(df)\exp\left[-3.2\left(\sum_i t_i x_i\right)^{0.63} - \sum_i s_i x_i - 0.3\right] \quad (7)$$

wherein $x_i$ is the thickness of a material i in the direction of irradiation and df is the distance between the point at which the energy fluence $\phi_p$ is observed and the focus of the X-ray source. The suffix p indicates that the primary radiation is concerned, i.e. the non-scattered radiation. In addition to primary radiation, scattered radiation also contributes to the energy fluence on the X-ray detector. A contribution by Rayleigh scattering, where the X-ray quanta are scattered without loss of energy through small angles, is given by:

$$\phi_r(di) = \phi_p(di) \, x_p \, \sigma_r (\sin \phi_m)^{E_r} \quad (8)$$

Therein:
 $\phi_r$ is the energy fluence of the Rayleigh scattered X-ray quanta in nJ mm$^{-2}$;
 di is the distance between the focus of the X-ray source 2 and the entrance screen of the X-ray image intensifier tube 5;
 $x_p$ is the thickness of the irradiated object in m;
 $\sigma_r$ is the linear interaction coefficient for Rayleigh scattering, for example 0.002 m$^{-1}$;
 $\phi_m$ is the angle between the object edge and the center of the X-ray detector; and
 Er is an experimentally determined constant value, for example Er=0.2. The model on which the equation (8) is based is a flat, homogeneous disc having an absorption equal to the absorption of water.

The following equation holds for Compton scattered X-rays where a loss of energy of the X-rays occurs:

$$\phi_c(dp) = \phi_p(dp) \, \tfrac{1}{2} s^2 \, x_p \, G/(s+at) \quad (9)$$

Therein, dp is the distance between the focus of the X-ray source 2 and the point at which the Compton radiation emerges from the irradiated object 7. The factor $\tfrac{1}{2}$ appears for thin objects, because Compton scattering is emitted to two sides. G is an experimentally determined factor which depends on the ratio of the thickness to the transverse dimension of the irradiated object and has a value of between 0.5 and 2.0, a being an experimentally determined constant term for which: a=0.6. For the Compton radiation $\phi_c$(di) reaching the X-ray detector the following is found:

$$\phi_c(di) = \phi_c(dp) \sin^2 (\phi_m) \quad (10)$$

Figure 6:
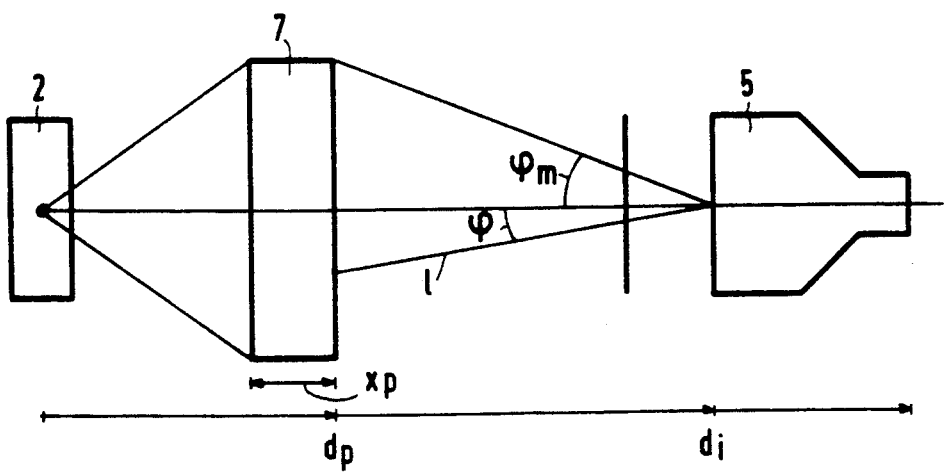
FIG. 6 is a diagram useful for explaining further principles of the present invention.

The factor $\sin^2 (\phi_m)$ is introduced because the Compton scattered X-rays leave the irradiated object, from the surface facing the X-ray detector, with an angular distribution which is given by $\cos(\phi)$. Therein, $\phi$ is the angle enclosed by the ray 1 in FIG. 6, extending between the surface emitting the Compton radiation and the center of the X-ray detector 5 with respect to the axis through the center of the X-ray detector. Integration over the disc-shaped proposed surface produces the term $\sin^2 (\phi_m)$.

From equations (7), (8) and (9) it follows for the energy fluence $\phi_s$(di) of the scattered X-rays on the detector that:

$$\begin{aligned}\phi_s(di) &= \phi_c(di) + \phi_r(di) = \phi_c(dp) \sin^2(\phi_m) + \\ &\quad \phi_p(di) \cdot x_p (\sin \phi_m)^{Er}\end{aligned} \quad (11)$$

$$\begin{aligned}\phi_s(di) &= \phi_p(dp) \, 1/2 \, s^2 \, x_p \, G \sin^2(\phi_m)/(s+at) + \\ &\quad \phi_p(di) \cdot x_p (\sin \phi_m)^{Er}\end{aligned}$$

wherein $\phi_p(dp)/\phi_p(di) = di^2/dp^2$, because of the inverse square attenuation, is applicable with equation (11):

$$\phi_s(di)/\phi_p(di) = \tfrac{1}{2} s^2 \, x_p \, G \sin^2(\phi_m)(di^2/dp^2)/(s+at) + x_p(\sin \phi_m)^{Er} \quad (12)$$

The radiation detected by the X-ray detector can be described as:

$$\phi_d(di) = \phi_p(di) + \phi_s(di) = \phi_p(di)(1 + \phi_s(di)/\phi_p(di))$$
$$\phi_d(di) = k(x_p)\,\phi_p(di) \quad (13)$$

Solution of equation (13), for example by iterative adaptation of the object thickness $x_p$, produces the thickness of the object $x_p$, after which the thickness of the absorption means required in order to obtain the desired attenuation can be calculated. When the desired thickness of the absorption means is known for the excessively light sub-areas in the X-ray image, the absorption means are translated and rotated by drive means 17 so that the projection of the part of the absorption means exhibiting the desired thickness is coincident with the relevant sub-area. It will be evident that the absorption means shown in FIG. 2 and in FIG. 5 can also be simultaneously used, the absorption means 24-27 and 43-46 then preferably being accommodated in the same housing 20.

I claim:

1. An X-ray examination apparatus, comprising an X-ray source for emitting an X-ray beam, an X-ray detector facing the X-ray source and responsive to incident X-rays from said beam to form an X-ray image of an object positioned between the X-ray source and the X-ray detector, a power supply system connected to the X-ray source to supply current and voltage to the X-ray source, absorption means which is both rotatable and linearly translatable to respective rotational and translational positions between the X-ray source and the X-ray detector to attenuate portions of the X-ray beam intercepted by said absorption means, and image processing means coupled to the X-ray detector for storing X-ray image absorption values in a matrix, said image processing means comprising detection means for determining a contour in the X-ray image outside of which the absorption values of sub-areas of the X-ray image are below a predetermined threshold value, arithmetic means for determining both the rotational and translational positions of the absorption means which would result in the absorption values in the sub-areas of the X-ray image outside said contour being increased to at least a predetermined value and the area of the rest of the image being minimum, and drive means coupled to the arithmetic means for rotating and translating the absorption means to the respective rotational and translational positions determined by the arithmetic means.

2. An X-ray examination apparatus as claimed in claim 1, wherein the absorption means comprises a first pair of slats having parallel, straight sides and being situated in a first plane extending transversely of the X-ray beam, said slats being translatable in the first plane in a direction transverse to the sides and being rotatable together in the first plane about an axis of rotation, and a second pair of slats having parallel straight sides and being situated in a second plane which extends parallel to the first plane, said second pair of slats being translatable in the second plane in a direction transverse to the sides of said second pair of slats and being rotatable together in the second plane about the axis of rotation.

3. An X-ray examination apparatus comprising:
   detector means for detecting X-ray radiation passed as a beam through an object under examination;
   rotatable and translatable absorption means positionable to rotational and translational positions to attenuate said radiation in a portion of said beam intercepted by said absorption means prior to said beam reaching said detecting means; and
   image processing means for processing the detected X-ray radiation for generating radiation absorption values manifesting an image of said object, said image having a given area;
   said image processing means comprising:
   detection means for determining a contour in said given area outside of which the radiation absorption values are below a predetermined threshold value; and
   arithmetic means responsive to said contour determining means for determining both the rotational and translational positions of the absorption means which would result in the absorption values in a portion of the image outside the contour being increased to a predetermined value and in the area of the rest of the image exclusive of said portion being minimum.

4. The apparatus of claim 3 further including drive means responsive to the arithmetic means for positioning the absorption means to the determined position.

5. The apparatus of claim 3 wherein the absorption means comprises first and second pairs of slats lying in respective first and second planes transverse said radiation, said first and second pairs of slats each being secured for translation in the respective planes and for rotation in said respective planes about respective axes.

6. The apparatus of claim 5 wherein the slats are secured for rotation about a common axis.

7. The apparatus of claim 3 wherein the absorption means exhibit locally varying absorption values.

8. The apparatus of claim 3 including control means responsive to said detection and arithmetic means for adjusting the power of said radiation as a function of exposure time value, voltage value and current value and for applying these values to said arithmetic means for said determining of the position of said absorption means.

9. An X-ray examination apparatus, comprising an X-ray source for emitting an X-ray beam, and X-ray detector facing the X-ray source and responsive to incident X-rays from said beam to form an X-ray image of an object positioned between the X-ray source and the X-ray detector, a power supply system connected to the X-ray source to supply current and voltage to the X-ray source, absorption means between the X-ray source and the X-ray detector to attenuate portions of the X-ray beam intercepted by the absorption means, and image processing means coupled to the X-ray detector for storing X-ray image absorption values in a matrix, said image processing means comprising detection means for detecting sub-areas in the X-ray image within which the absorption values are below a predetermined threshold value, arithmetic means for determining a position of the absorption means which would result in the absorption values in the detected sub-areas of the X-ray image being increased to a predetermined value, and drive means coupled to the image processing means for displacing the absorption means to the position determined by the image processing means, wherein the absorption means comprises a first pair of slats having parallel, straight sides and being situated in a first plane extending transversely of the X-ray beam, said slats being translatable in the first plane in a direction transverse to the sides and being rotatable together in the first plane about an axis of rotation, and a second pair of slats having parallel straight sides and being situated in a second plane which extends parallel to the first plane, said second pair of slats being translatable in the second plane in a direction transverse to the sides of said second pair of slats and being rotatable together in the second plane about the axis of rotation.

10. An X-ray examination apparatus as claimed in claim 9, in which the first and second pairs of slats are shaped as a wedge, said drive means being for translating said first and second pairs of slats in said first and second planes, respectively.

* * * * *